United States Patent
Reid et al.

(10) Patent No.: US 8,912,746 B2
(45) Date of Patent: Dec. 16, 2014

(54) SURGICAL INSTRUMENT MOTOR PACK LATCH

(71) Applicant: Intuitive Surgical Operations, Inc., Sunnyvale, CA (US)

(72) Inventors: Robert Cyrus Reid, San Francisco, CA (US); John W. Zabinski, Fremont, CA (US); Alan Eton Loh, Los Altos, CA (US); Bruce M. Schena, Menlo Park, CA (US); David W. Weir, Emerald Hills, CA (US); Gregory W. Dachs, II, San Mateo, CA (US); David W. Bailey, Portola Valley, CA (US); Melody Wu, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 230 days.

(21) Appl. No.: 13/662,390

(22) Filed: Oct. 26, 2012

(65) Prior Publication Data

US 2013/0110129 A1     May 2, 2013

Related U.S. Application Data

(60) Provisional application No. 61/551,873, filed on Oct. 26, 2011, provisional application No. 61/560,203, filed on Nov. 15, 2011.

(51) Int. Cl.
| | | |
|---|---|---|
| *B25J 9/18* | (2006.01) | |
| *A61B 19/00* | (2006.01) | |
| *A61B 17/29* | (2006.01) | |
| *A61B 17/00* | (2006.01) | |

(52) U.S. Cl.
CPC .............. *A61B 19/2203* (2013.01); *A61B 17/29* (2013.01); *A61B 2019/2215* (2013.01); *A61B 2019/2223* (2013.01); *A61B 2017/00477* (2013.01)
USPC ................... 318/568.11; 318/568.1; 318/567; 318/560

(58) Field of Classification Search
CPC ................................................... A61B 19/2203
USPC ......................... 318/568.11, 568.1, 567, 560
See application file for complete search history.

(56) References Cited

U.S. PATENT DOCUMENTS

| | | | |
|---|---|---|---|
| 5,710,870 A * | 1/1998 | Ohm et al. ..................... 700/263 |
| 8,444,631 B2 * | 5/2013 | Yeung et al. ...................... 606/1 |
| 2006/0074415 A1 | 4/2006 | Scott et al. |
| 2009/0099520 A1 | 4/2009 | Millman et al. |
| 2011/0015650 A1 | 1/2011 | Choi et al. |

FOREIGN PATENT DOCUMENTS

| | | |
|---|---|---|
| EP | 1815950 A1 | 8/2007 |
| WO | WO-2008086493 A2 | 7/2008 |
| WO | WO-2011143020 A1 | 11/2011 |

OTHER PUBLICATIONS

International Preliminary Report on Patentability and Written Opinion for Application No. PCT/US2012/062298, mailed on Apr. 29, 2014, 5 pages.
International Search Report for Application No. PCT/US2012/062298, mailed on May 15, 2013, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — David S Luo

(57) ABSTRACT

A latch mechanism selectively retains a first assembly to a second assembly. The first and second assemblies are configured for sliding engagement along an engagement axis. The latch mechanism includes a latch shaft mounted to the first assembly to rotate about a latch shaft axis, a torsion spring to bias the latch shaft relative to the first assembly, and a transverse latch member coupled with the second assembly. The latch mechanism is configured to automatically latch in response to the first assembly being pushed toward the second assembly. The transverse latch member interacts with the latch shaft to rotate the latch shaft in a first direction in response to movement of the first assembly toward the second assembly. Further motion of the first assembly toward the second assembly results in rotation of the latch shaft opposite to the first direction into a retention configuration that retains the transverse latch member.

24 Claims, 15 Drawing Sheets

SURGICAL INSTRUMENT MOTOR PACK LATCH

This application claims the benefit of U.S. Provisional Application No. 61/551,873, filed Oct. 26, 2011, and U.S. Provisional Application No. 61/560,203, filed Nov. 15, 2011, the entireties of which are incorporated by reference herein.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting instruments, including known surgical staplers, have opposing jaws that clamp tissue and an articulated knife to cut the clamped tissue.

The operation of a surgical stapler typically involves the transfer of a relatively high amount of power to the end effector of the surgical stapler. For example, using an exemplary surgical stapler, the clamping of tissue can involve the transfer of approximately 11 Watts of power for 4 seconds; the stapling and cutting of the clamped tissue can involve the transfer of approximately 37 Watts of power for 6 seconds. One way of transferring such power levels involves transferring rotary actuation motion from electric motors to the end effector via drive shafts. Such an actuation system, however, can include high cost drive train components, which increase the cost of the surgical instrument.

Thus, there is believed to be a need for surgical instruments that incorporate rotational drive train components in a cost effective manner.

BRIEF SUMMARY

A mechanism for latching assemblies together is disclosed. While the latch mechanism is described herein in the context of surgical instruments, the latch mechanism can be used to latch together any suitable assemblies. In the described embodiments, surgical instruments are disclosed in which high cost drive train components are embodied in a motor pack that is detachably mountable to a proximal chassis of a surgical instrument. The motor pack and the proximal chassis include complementary-shaped interface features that provide for sliding engagement between the motor pack and the chassis. A latch mechanism provides for automatic latching of the motor pack to the chassis in response to sliding of the motor pack onto the chassis. The latch mechanism includes a spring-loaded latch shaft mounted to rotate about a latch axis. The latch shaft interfaces with a transverse latch member, which causes the latch shaft to rotate in response to movement of the motor pack toward the chassis culminating in the latch shaft blocking movement of the latch transverse member to retain the motor pack to the chassis. The motor pack can be demounted from the chassis by rotating the latch shaft to orient the latch shaft to permit movement of the transverse latch member relative to the latch shaft.

Thus, in one aspect, a robotic surgical assembly is provided. The surgical assembly includes an end effector including an articulated feature, an elongate instrument shaft having a distal end supporting the end effector and a proximal end, a chassis supporting the instrument shaft proximal end, a motor pack detachably mountable to the chassis, and a latch mechanism configured to selectively retain the motor pack to the chassis. The chassis is detachably mountable to a robotic arm. The chassis includes an actuation input drivingly coupled with the end effector articulated feature. The motor pack includes an actuation output that drivingly couples with the chassis actuation input when the motor pack is mounted to the chassis. The motor pack and the chassis have complementary-shaped interfaces providing sliding engagement between the motor pack and the chassis along an engagement axis. The latch mechanism includes a latch shaft, a torsion spring, and a transverse latch member. The latch shaft is mounted to one of the motor pack or the chassis to rotate about a latch shaft axis. The torsion spring is operably coupled with the latch shaft to bias the latch shaft into a pre-engagement orientation relative to the one of the motor pack or the chassis when the motor pack is not mounted to the chassis. The transverse latch member is mounted to the other one of the motor pack or the chassis. The transverse latch member is oriented transverse to the latch shaft axis when the motor pack is slidingly engaged with the chassis along the engagement axis. The transverse latch member interfaces with the latch shaft to rotate the latch shaft about the latch shaft axis in a first rotational direction in response to relative movement of the motor pack toward the chassis along the engagement axis from a pre-engagement configuration to an intermediate configuration. The latch shaft is configured to rotate opposite to the first direction in response to relative movement of the motor pack toward the chassis along the engagement axis from the intermediate configuration to a retention configuration. The latch shaft blocks movement of the transverse latch member in the retention configuration to restrain the motor pack from moving away from the chassis along the engagement axis. In many embodiments, the latch shaft axis and the engagement axis are parallel.

The latch shaft can be mounted to either the motor pack or the chassis. For example, in many embodiments, the latch shaft is mounted to the motor pack for rotation relative to the motor pack about the latch shaft axis; the torsion spring is coupled with motor pack; and the transverse latch member is coupled with the chassis. And in many other embodiments, the latch shaft is mounted to the chassis for rotation relative to the chassis about the latch shaft axis; the torsion spring is coupled with chassis; and the transverse latch member is coupled with the motor pack.

In many embodiments, the latch shaft includes a cylindrical portion having a transverse slot. The transverse slot is configured to accommodate the transverse latch member and interface with the transverse latch member during at least part of the relative movement between the motor pack and the chassis along the engagement axis from the pre-engagement configuration through the intermediate configuration to the retention configuration.

In many embodiments, the latch mechanism is configured to impart a retaining tension between the motor pack and the chassis. For example, in many embodiments the transverse slot interfaces with the transverse latch member in the retention configuration to impart a force component to the transverse latch member along the latch shaft axis to retain the motor pack to the chassis.

In many embodiments, the transverse latch member is configured to interface with the latch shaft via rolling contact. For example, the transverse latch member can include a first rolling element that interfaces with the latch shaft via rolling contact. And in many embodiments, the transverse latch member further includes a second rolling element that interfaces with the latch shaft via rolling contact. The first and second latch rolling elements can be configured to rotate in different directions.

In many embodiments, the latch mechanism includes a disengagement feature operable to rotate the latch shaft in the first rotational direction to an orientation in which the motor pack can be moved relative to the chassis from the retention configuration to the intermediate configuration. In many embodiments, the disengagement feature includes a hand rotatable member rotationally coupled with the latch shaft.

In many embodiments, the chassis and the motor pack are configured to allow the motor pack to be mounted to the chassis without first ensuring that the motor pack actuation output is angularly aligned with the chassis actuation input. For example, at least one of the chassis actuation input or the motor pack actuation output can include a spring loaded coupling feature that accommodates an initial coupling misalignment between the chassis actuation input and the motor pack actuation output.

In many embodiments, the surgical assembly includes a sensor to verify that the motor pack is mounted to the chassis. For example, the surgical assembly can include a sensor mounted to the motor pack or the chassis configured to generate a signal indicative of the motor pack being mounted to the chassis in the retention configuration.

In many embodiments, the surgical assembly includes an ejection mechanism that serves to make the state of the coupling between the motor pack and the chassis obvious to the user. For example, the ejection mechanism can be configured to maintain at least a minimum gap between the motor pack and the chassis absent the motor pack and the chassis being pushed together by a force sufficient to reconfigure the ejection mechanism.

In another aspect, a latch mechanism is provided. The latch mechanism selectively prevents separation between a first assembly and a second assembly. The first and second assemblies have complementary-shaped interfaces providing sliding engagement between the first and second assemblies along an engagement axis. The latch mechanism includes a latch shaft mounted to the first assembly to rotate about a latch shaft axis relative to the first assembly, a torsion spring coupled with the latch shaft and the first assembly to bias the latch shaft into a pre-engagement orientation relative to the first assembly, and a transverse latch member coupled with the second assembly. The transverse latch member is oriented transverse to the latch shaft axis when the first and second assemblies are slidingly engaged along the engagement axis. The transverse latch member interfaces with the latch shaft to rotate the latch shaft relative to the first assembly about the latch shaft axis in a first rotational direction in response to relative movement of the first assembly toward the second assembly along the engagement axis from a pre-engagement configuration to an intermediate configuration. The latch shaft is configured to rotate opposite to the first rotational direction relative to the first assembly in response to relative movement of the first assembly toward the second assembly from the intermediate configuration to a retention configuration. The latch shaft blocks movement of the transverse latch member in the retention configuration to restrain the first member from moving away from the second assembly along the engagement axis. In many embodiments, the latch shaft axis and the engagement axis are parallel.

In many embodiments of the latch mechanism, the latch shaft includes a cylindrical portion having a transverse slot. The transverse slot is configured to accommodate the transverse latch member and interface with the transverse latch member during at least part of the relative movement between the first and second assemblies along the engagement axis from the pre-engagement configuration through the intermediate configuration to the retention configuration.

In many embodiments, the latch mechanism is configured to impart a retaining tension between the first and second assemblies. For example, in many embodiments the transverse slot interfaces with the transverse latch member in the retention configuration to impart a force component to the transverse latch member along the latch shaft axis to retain the first assembly to the second assembly.

In many embodiments of the latch mechanism, the transverse latch member is configured to interface with the latch shaft via rolling contact. For example, the transverse latch member can include a first rolling element that interfaces with the latch shaft via rolling contact. And in many embodiments, the transverse latch member further includes a second rolling element that interfaces with the latch shaft via rolling contact. The first and second latch rolling elements can be configured to rotate in different directions.

In many embodiments, the latch mechanism includes a disengagement feature operable to rotate the latch shaft in the first rotational direction to an orientation in which the first assembly can be moved relative to the second assembly from the retention configuration to the intermediate configuration. In many embodiments, the disengagement feature includes a hand rotatable member rotationally coupled with the latch shaft.

In many embodiments, the latch mechanism includes an ejection mechanism that serves to make the state of the coupling between the first and second assemblies obvious to the user. For example, the ejection mechanism can be configured to maintain at least a minimum gap between the first and second assemblies absent the first and second assemblies being pushed together by a force sufficient to reconfigure the ejection mechanism.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
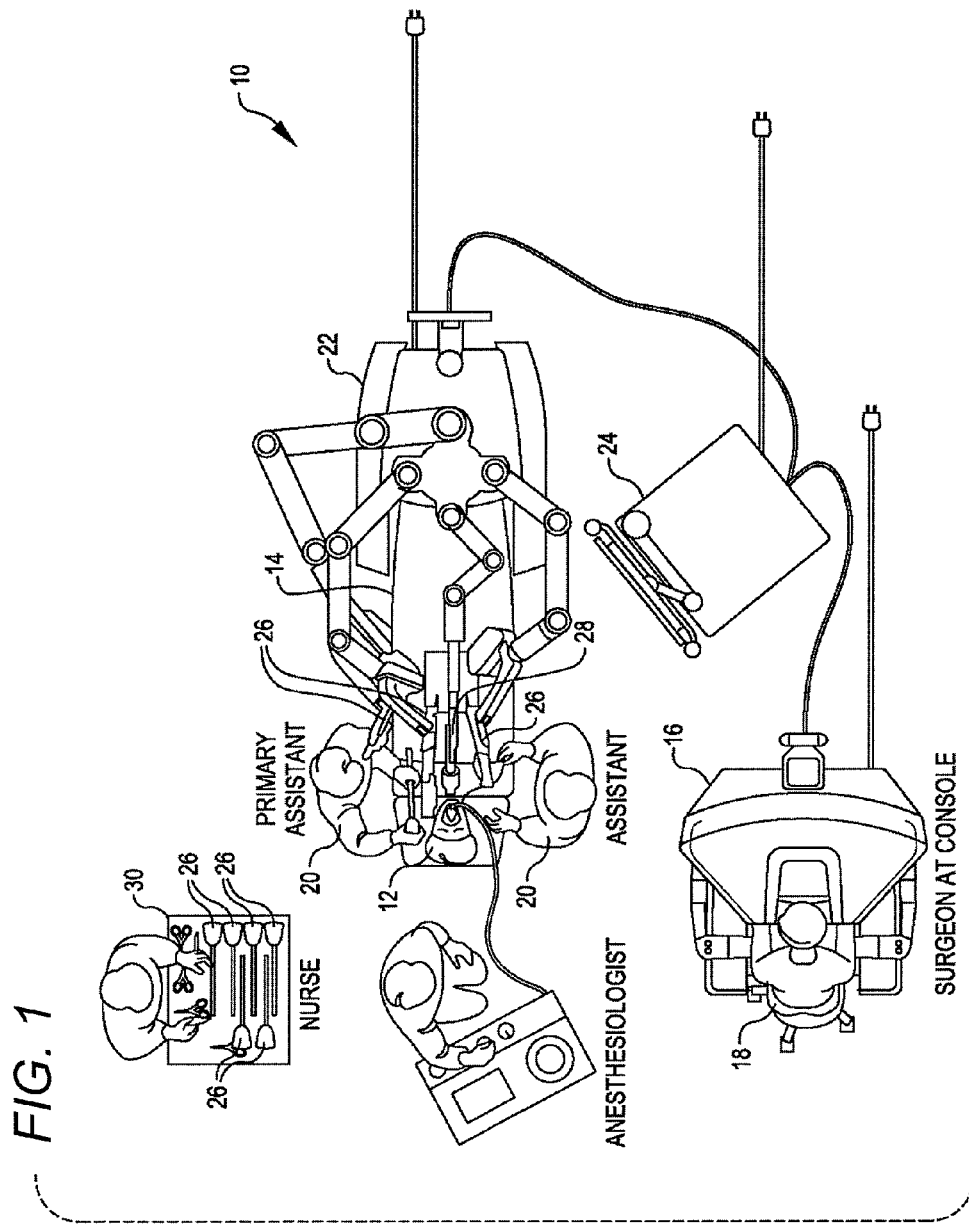
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
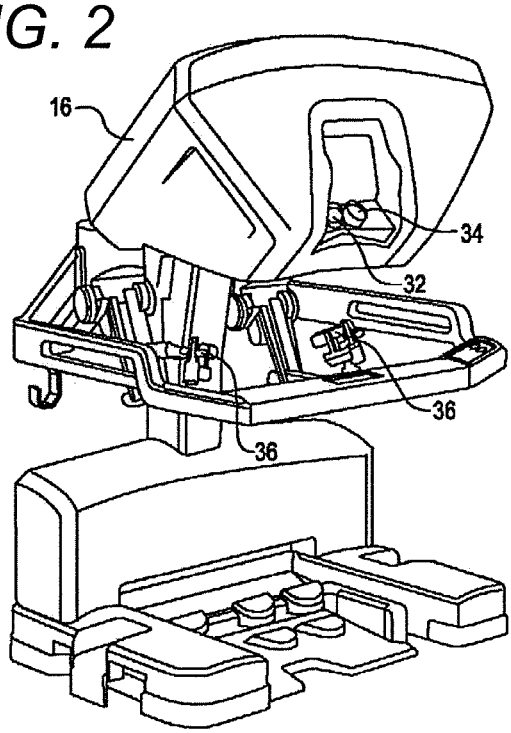
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
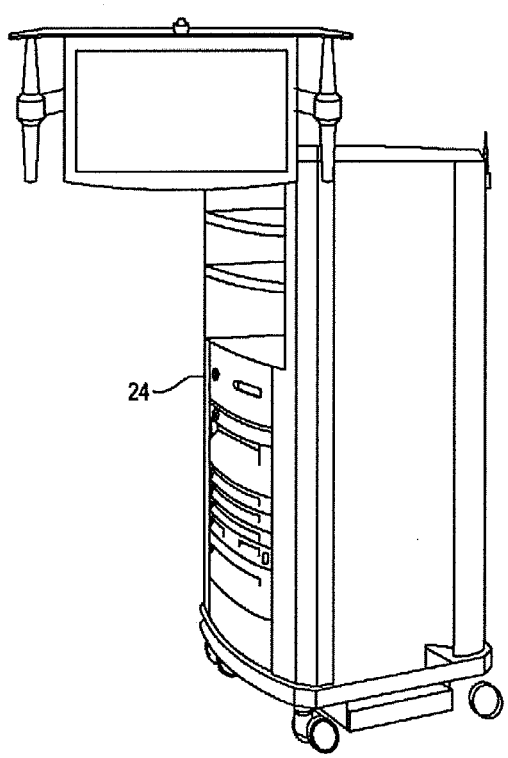
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
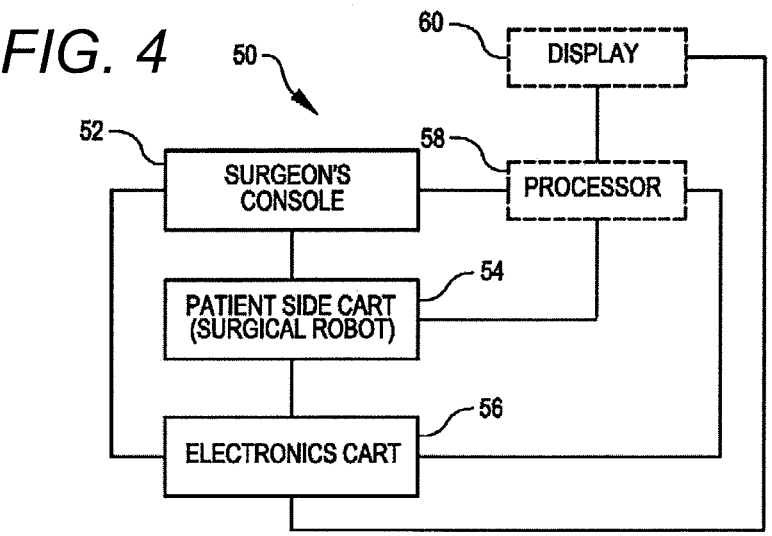
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
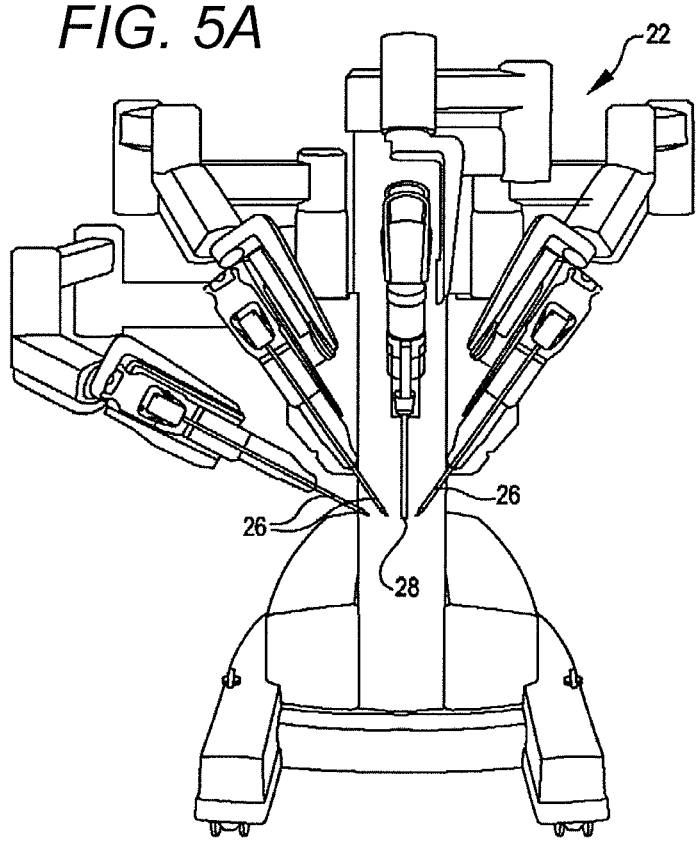
FIG. 5A is a front view of a patient side cart (surgical robot) of a robotic surgery system, in accordance with many embodiments.
Figure 5B:
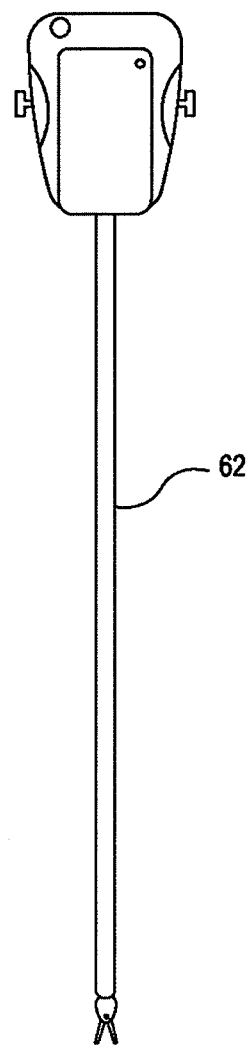
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical Tools with Latching Motor Pack

Figure 6A:
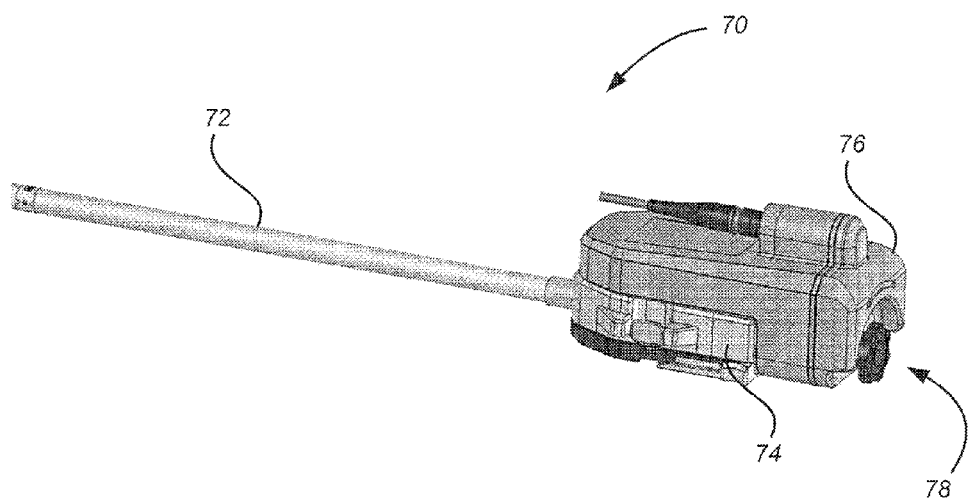
FIG. 6A is a perspective view of a robotic surgical tool in which a motor pack is mounted to a proximal chassis, in accordance with many embodiments.

FIG. 6A shows a robotic surgical tool 70, in accordance with many embodiments. The surgical tool 70 includes a elongate instrument shaft 72 supporting an end effector (not shown) at a distal end of the instrument shaft 72, a proximal chassis 74 supporting the proximal end of the instrument shaft 72, and a motor pack 76 mounted and latched to the proximal chassis 74. The motor pack 76 includes electric motors that are drivingly coupled with articulated features of the end effector. A latch mechanism 78 is used to selectively retain the motor pack 76 to the proximal chassis 74.

Figure 6B:
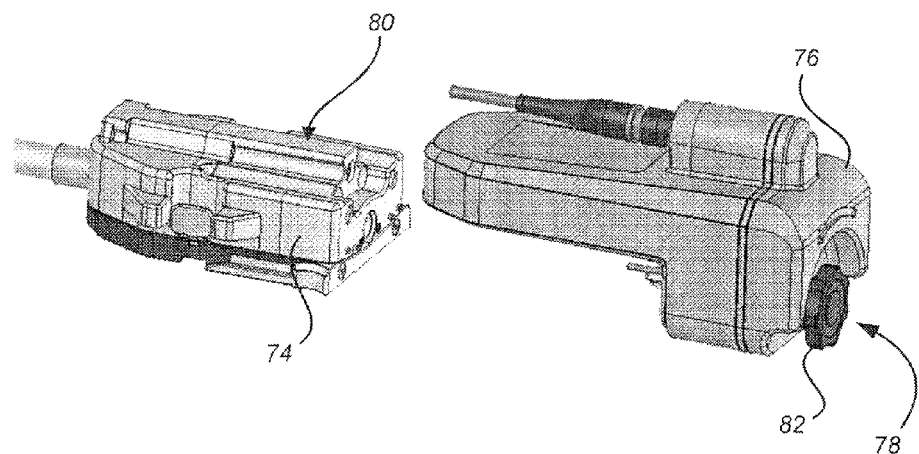
FIG. 6B is a perspective view of the robotic surgical tool of FIG. 6A showing the motor pack separated from the proximal chassis.

FIG. 6B shows the motor pack 76 separated from the proximal chassis 74. The top of the proximal chassis 74 includes a longitudinally-oriented dovetail alignment feature 80 that interfaces with a complementarily-shaped dovetail alignment feature of the motor pack 76 to provide for sliding engagement between the motor pack 76 and the proximal chassis 74 about a longitudinally-oriented engagement axis. The latch mechanism 78 includes a disengagement feature 82 that can be rotated to unlatch the motor pack 76 from the proximal chassis 74.

Figure 7:
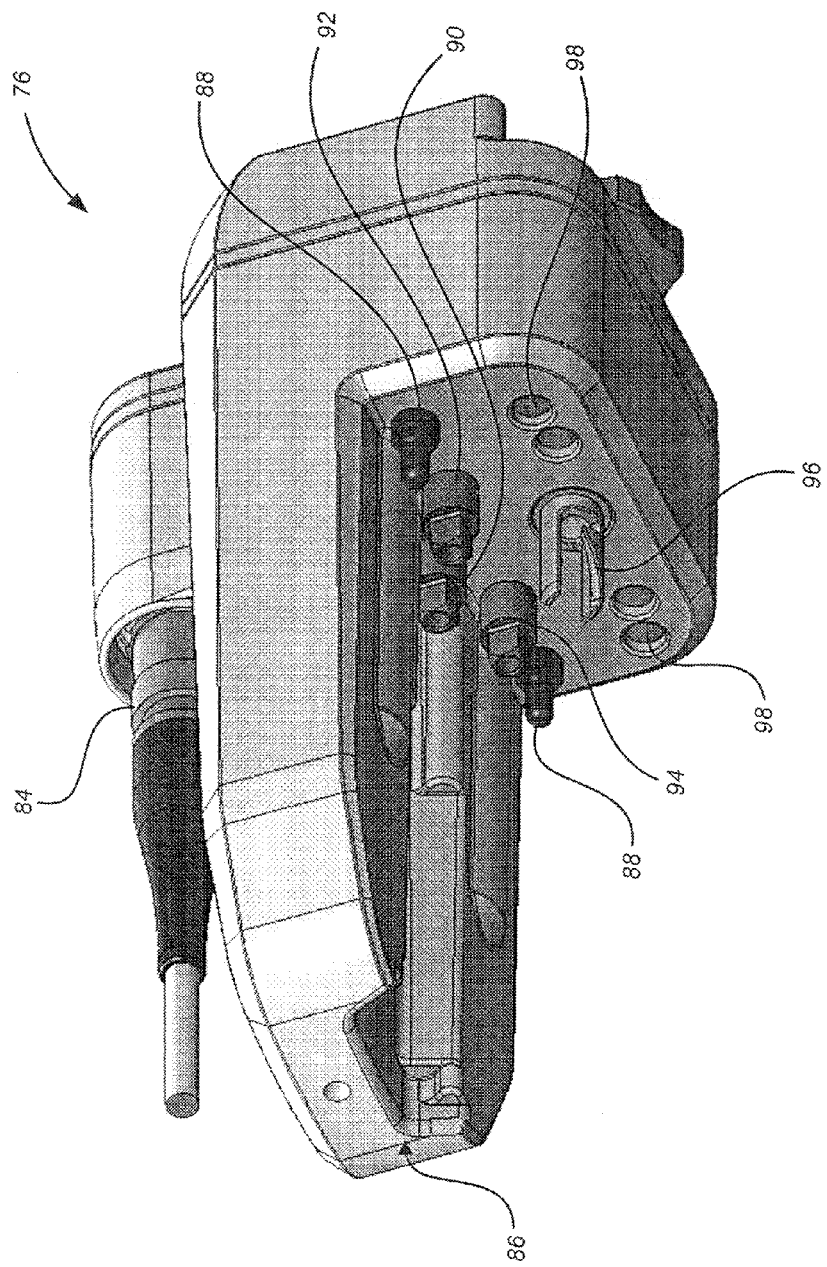
FIG. 7 is a perspective view of the motor pack of FIG. 6A.

FIG. 7 shows interfacing features of the motor pack 76. A control cable 84 electrically connects the motor pack 76 to a controller (not shown). The control cable 84 is detachably mountable to the motor pack 76 via an electrical connector. The dovetail alignment feature 86 of the motor pack 76 interfaces with the dovetail alignment feature 80 of the proximal chassis 74. Precision alignment pins 88 are received by corresponding alignment receptacles in the proximal chassis 74. A roll drive coupling 90, a clamp drive coupling 92, and a fire drive coupling 94 interface with corresponding input couplings of the proximal chassis 74. The roll drive coupling 90 is rotationally coupled with rotation of the instrument shaft 72. The clamp drive coupling 92 is used to transfer a rotary actuation motion from an electric motor in the motor pack 76 to a clamping mechanism in the end effector. The fire drive coupling 94 is used to transfer a rotary actuation motion from an electric motor in the motor pack 76 to the end effector to deploy staples into clamped tissue and to articulate a knife to cut the clamped and stapled tissue. A latch shaft 96 of the latch mechanism is configured to provide for automated latching of the motor pack 76 to the proximal chassis 74 in response to pushing the motor pack 76 onto the proximal chassis 74 along the engagement axis. Motor pack electrical contacts 98 are positioned to interface with corresponding proximal chassis electrical contacts when the motor pack 76 is mounted and latched to the proximal chassis 74.

The surgical tool 70 can be configured to be a cardiac floating (Type CF) device for safe direct cardiac application by the end effector. Accordingly, the roll drive coupling 90, clamp drive coupling 92, fire drive coupling 94, and latch mechanism 78 are configured to be electrically isolated from power components within the motor pack 76, which in turn is grounded in case of shorting. In some embodiments, exterior housings of the surgical tool 70 and motor pack 76, all or supporting portions of the drive couplings and latch mechanism 78 of the motor pack 76, and/or corresponding cooperative portions of the surgical tool 70 are constructed from a non-conductive material, such as a polymer material, such that all connecting portions of the surgical tool 70 and motor pack are electrically isolated.

Figure 8:
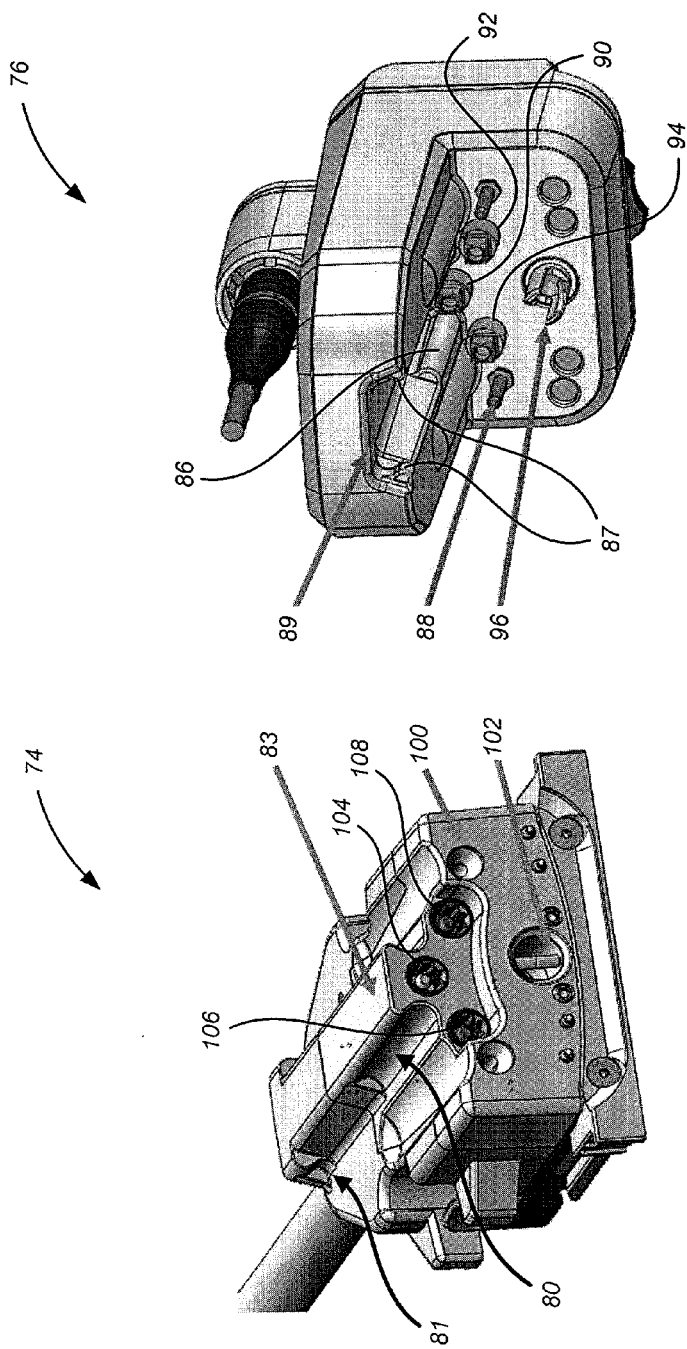
FIG. 8 is a perspective view of the robotic surgical tool of FIG. 6A showing interfacing features of the proximal chassis and the motor pack.

FIG. 8 shows corresponding interfacing features of the proximal chassis 74 and the motor pack 76 that provide progressive engagement during the mounting of the motor pack 76 on to the chassis 74 for easy, precise alignment. Easy initial engagement between the motor pack 76 and the proximal chassis 74 is provided by double-dove tail features of the motor pack 76 and the proximal chassis 74. The double-dovetail features of the proximal chassis 74 include a pair of proximal recesses 80, a pair of distal recesses 81, and a flat top surface 83 disposed over and between the proximal recesses 80 as well as over and between the distal recesses 81. The double-dovetail features of the motor pack 76 include a pair of elongated proximal protrusions 86, a pair of distal protrusions 87, and a flat surface 89 disposed over and between the proximal protrusions 86 as well as over and between the distal protrusions 87. When the motor pack 76 is fully mounted to the proximal chassis 74, the distal protrusions 87 are received by the distal recesses 81 and the proximal protrusions 86 are received by the proximal recesses 80, thereby securing the motor pack 76 to the proximal chassis 74 against all relative motion except proximal translation of the motor pack 76 relative to the proximal chassis 74. The gap between the proximal protrusions 86 and the distal protrusions 87 facilitates a coupling sequence in which the motor pack 76 is partially overlapped with the proximal chassis 74 so that the motor pack flat surface 89 interfaces with the proximal chassis top surface 83 and the proximal protrusions 86 are disposed proximal of the proximal chassis proximal recesses 80. The motor pack 76 is then slid distal relative to the proximal chassis 74, thereby causing the proximal protrusions 86 to be slidingly received by the proximal recesses 80. During a final portion of distal movement of the motor pack 76 relative to the proximal chassis 74 the distal protrusions 87 are then received by the distal recesses 81. The double-dovetail features accommodate a range of initial misalignment between the motor pack 76 and the proximal chassis 74, thereby making it easy to accomplish the initial mating between the double-dovetail features. Once initially mated, relative motion of the motor pack 76 toward the proximal chassis 74 results in progressively less possible misalignment between the motor pack 76 and the proximal chassis 74 due to the progressively longer interfacing portions of the double-dovetail features. At the end of the relative movement of the motor pack 76 toward the proximal chassis 74, the precision alignment pins 88 on the motor pack 76 engage the precision alignment receptacles 100 in the proximal chassis 74, thereby precisely positioning the motor pack 76 relative to the proximal chassis 74. The latch mechanism 78 includes the latch shaft 96 mounted to the motor pack 76 and a transverse latch member 102 mounted to the proximal chassis 74. The latch shaft 96 interfaces with the transverse latch member 102 to retain the motor pack 76 to the proximal chassis 74. When in the retention configuration, the motor pack output couplings 90, 92, 94 engage corresponding proximal chassis input couplings 104, 106, 108, respectively.

Figure 9:
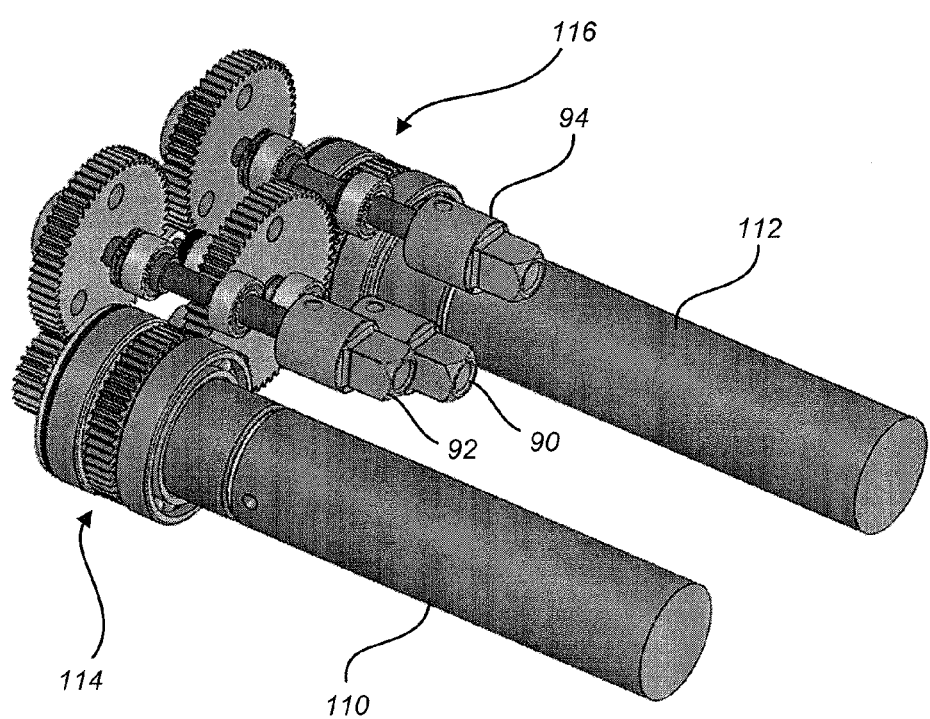
FIG. 9 is a perspective view of internal components of the motor pack of FIG. 6A.

FIG. 9 shows actuation drive train components disposed in the motor pack 76. The drive train components include a clamp motor 110 rotationally coupled with the clamp drive coupling 92, and a fire motor 112 rotationally coupled with the fire drive coupling 94. The drive train components further include a clamp differential 114 and a fire differential 116, each of which receive rotation input from the instrument shaft 72 via the roll drive coupling 90. The clamp differential 114 combines the received instrument shaft rotational feedback with the output of the clamp motor 110 to generate the rotational motion transferred to the clamp drive coupling 92. Likewise, the fire differential 116 combines the received instrument shaft rotational feedback with the output of the fire motor 112 to generate the rotational motion transferred to the fire drive coupling 94. Due to the sophistication and the corresponding expense of the drive train components, locating these drive train components in the motor pack 76 serves to reduce the expense of the surgical instrument 70 by allowing the drive train components to be reused in combination with different proximal chassis 74.

Figure 10A:
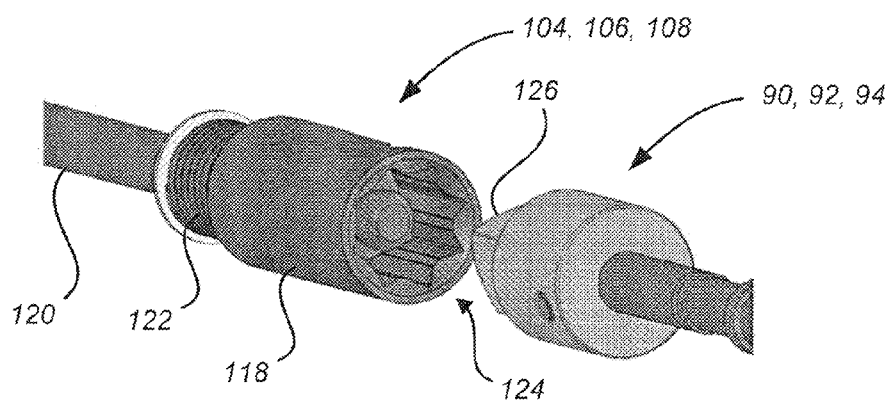
FIGS. 10A through 10C illustrate actuation coupling features of the robotic surgical tool of FIG. 6A.
Figure 10B:
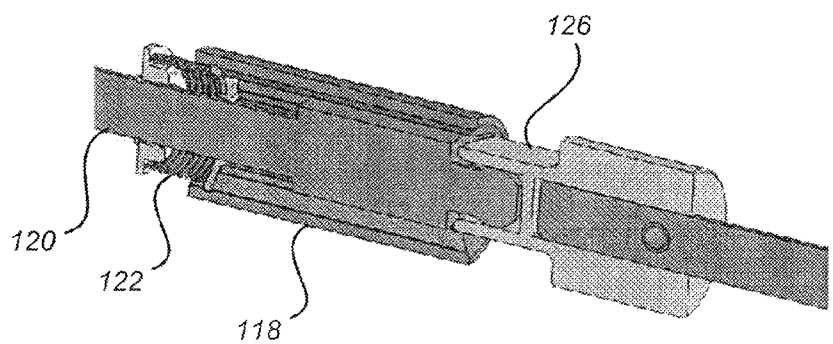
Figure 10C:
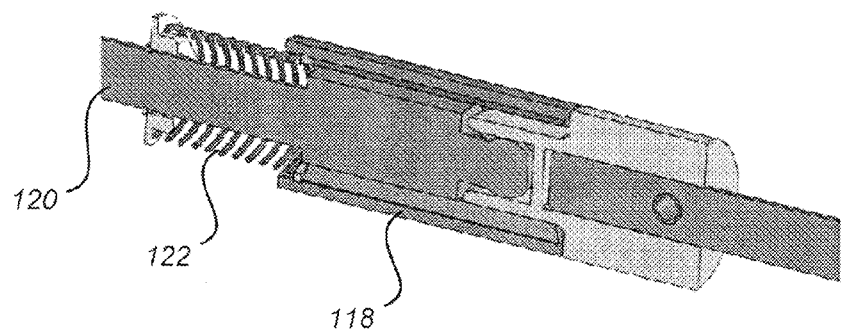

FIGS. 10A through 10C illustrate actuation coupling features of the robotic surgical tool 70. FIG. 10A shows a proximal chassis input coupling (one of input couplings 104, 106, 108) offset from a motor pack output coupling (one of output couplings 90, 92, 94). The proximal chassis input coupling includes an external coupling member 118 that is slidingly mounted and rotationally tied (e.g., by splines) to a drive shaft 120. The proximal chassis input coupling further includes a compression spring 122 that biases the external coupling member 118 into an extended configuration relative to the drive shaft 120. The external coupling member 118 provides a female coupling receptacle 124 that is shaped to receive and rotationally couple with the motor pack output coupling. The motor pack output coupling includes a male coupling 126 that is received within and rotationally couples with the external coupling member 118.

The actuation coupling features are configured to tolerate initial misalignment between the proximal chassis input couplings and the motor pack output couplings. FIG. 10B shows an initial configuration that arises when initial misalignment prevents reception of the male coupling 126 within the female coupling receptacle 124 of the external coupling member 118. The resulting contact between the male coupling 126 and the external coupling member 118 translates the external coupling member 118 relative to the drive shaft 120, thereby compressing the compression spring 122. In many embodiments, a subsequent homing sequence in which the motor pack output couplings are rotated is used to produce alignment between the male coupling 126 and the female coupling receptacle 124, during which the compression spring 122 serves to translate the external coupling member 118 relative to the drive shaft 120 to receive the male coupling 126 resulting in the engaged configuration illustrated in FIG. 10C.

Figure 11A:
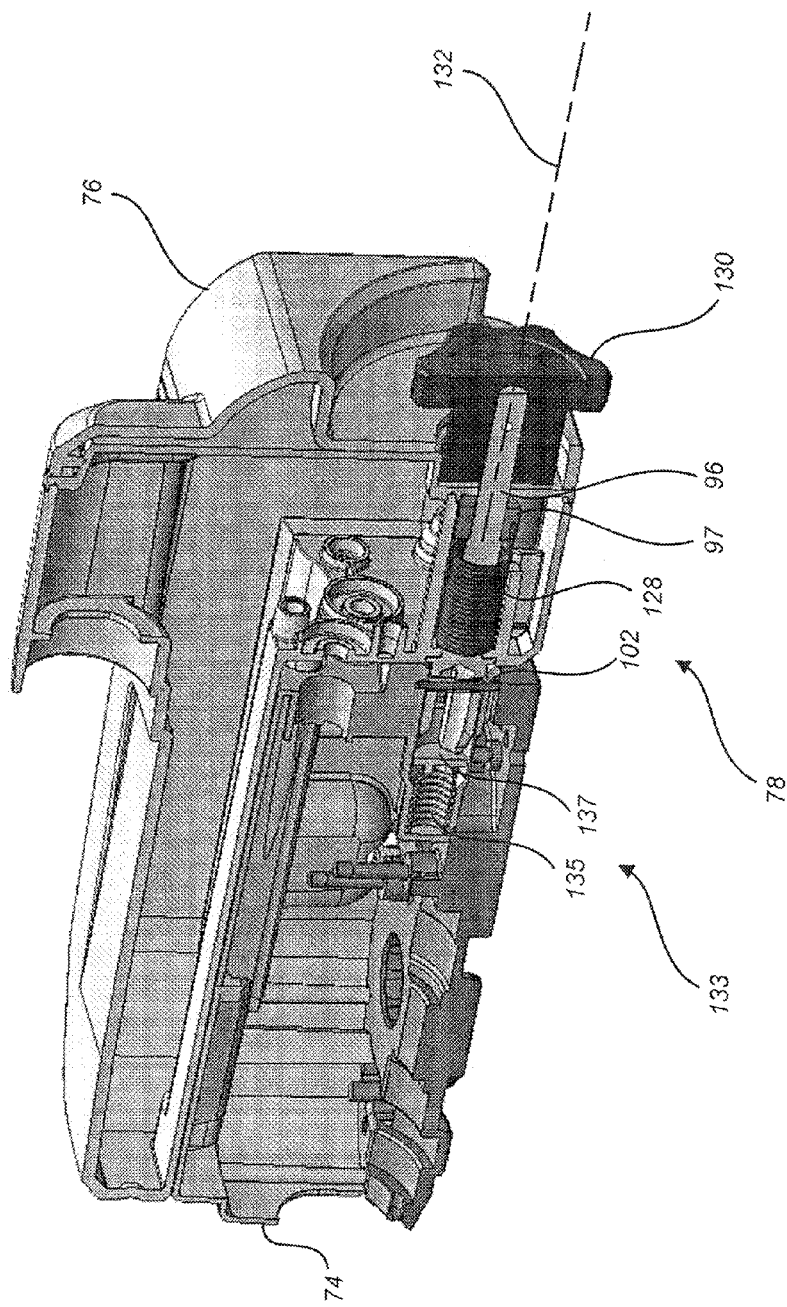
FIG. 11A is a cross-sectional perspective view of the robotic surgical instrument of FIG. 6A showing details of a latch mechanism used to retain the motor pack to the proximal chassis.

FIG. 11A shows details of the latch mechanism 78 used to retain the motor pack 76 to the proximal chassis 74. The latch mechanism 78 includes the latch shaft 96, a torsion spring 128, the transverse latch member 102, and a disengagement feature 130. The latch shaft 96 is mounted to the motor pack 76 to rotate about a latch shaft axis 132. The torsion spring 128 is coupled between the latch shaft 96 and the motor pack 76 and biases the latch shaft 96 into a pre-engagement orientation relative to the motor pack 76 when the motor pack 76 is not mounted to the proximal chassis 74. A clocking component 97 is coupled with the latch shaft 96 to rotate with the latch shaft 96. The clocking component 97 has a portion that is non-axially symmetric to the latch shaft axis 132. The non-axially symmetric portion is held in contact with an inner wall of the motor pack 76 by the torsion spring 128 when the motor pack 76 is not mounted to the proximal chassis 74, thereby biasing the latch shaft 96 into the pre-engagement orientation. The latch shaft 96 interfaces with the transverse latch member 102 to retain the motor pack 76 to the proximal chassis 74. The disengagement feature 130 can be rotated to orient the latch shaft 96 to release the transverse latch member 102, thereby allowing the motor pack 76 to be demounted from the proximal chassis 74.

The proximal chassis 74 includes an ejection mechanism 133 that serves to make the state of the coupling between the motor pack 76 and the proximal chassis 74 obvious to the user. The ejection mechanism 133 includes a compression spring 135 and a spring cap 137. The compression spring 135 and the spring cap 137 are disposed within a receptacle of the proximal chassis 74. The proximal portion of the receptacle is sized to accommodate the distal end of the latch shaft 96 and the spring cap 137. The distal portion of the receptacle is sized to accommodate the compression spring 135. The compression spring 135 interfaces at its distal end with an end wall of the receptacle and at its proximal end with the spring cap 137. The spring cap 137 also interfaces with the distal end of the latch shaft 96. In the latched configuration shown in FIG. 11A in which the motor pack 76 is latched to the proximal chassis 74, the compression spring 135 is in a compressed state as a result of the presence of the latch shaft 96. In the latched configuration, the force from the compression spring 135 is transferred into the distal end of the latch shaft 96 and reacted by the transverse latch member 102.

Figure 11B:
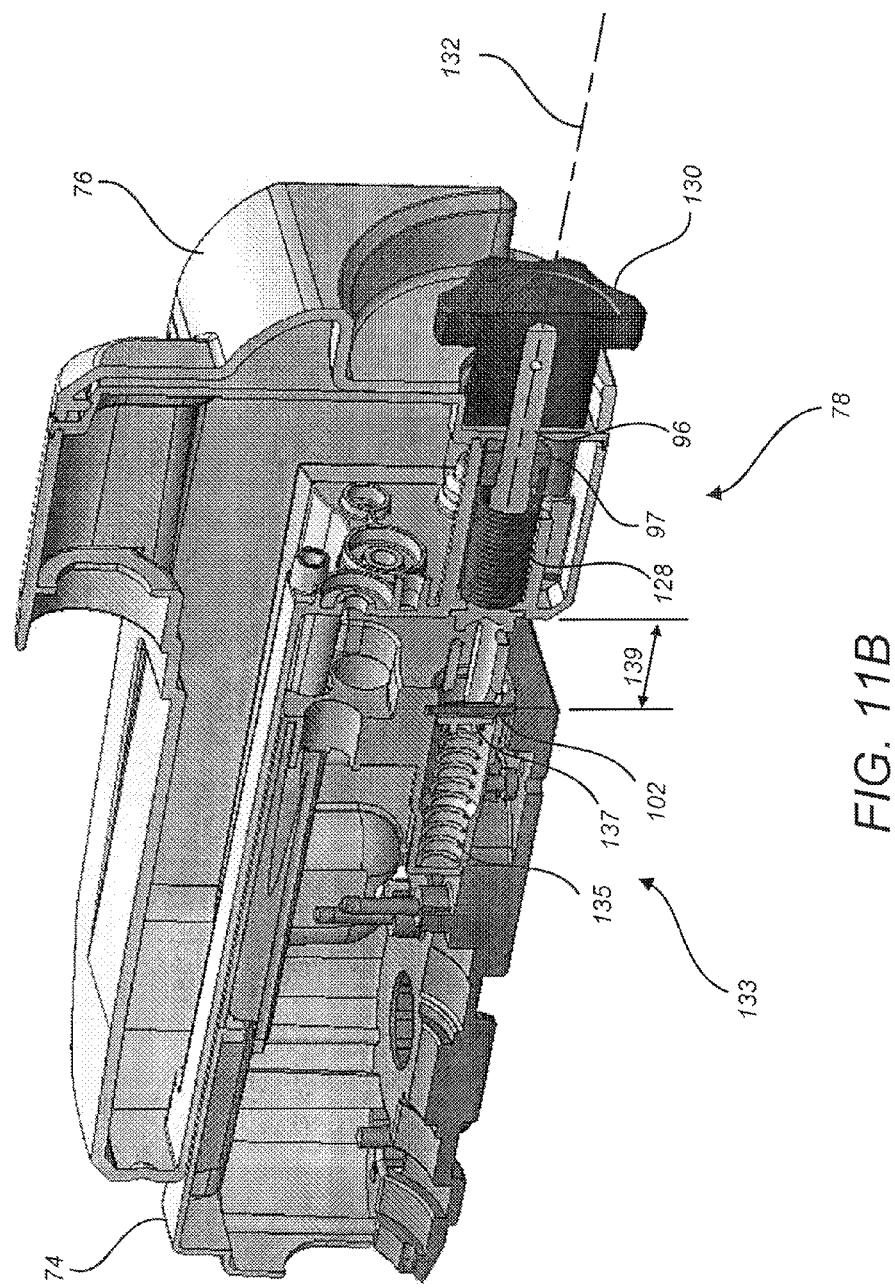
FIG. 11B is a cross-sectional perspective view of the robotic surgical instrument of FIG. 6A showing the motor pack in an unlatched position relative to the proximal chassis.

FIG. 11B shows the motor pack 76 and the proximal chassis 74 in an unlatched configuration. In this unlatched configuration, the motor pack 76 and the proximal chassis 74 are slidingly coupled via the dove tail features 80, 86, but not latched via the latch mechanism 78. Also in this unlatched configuration, the compression spring 135 is in a compressively-preloaded state. The compression spring 135 and the spring cap 137 are constrained between the end wall of the receptacle and the transverse latch member 102. In the absence of the motor pack 76 being pushed towards the proximal chassis 74 with sufficient force to compress the compression spring 135, a minimum gap 139 is maintained between the motor pack 76 and the proximal chassis 74, thereby rendering the unlatched configuration more obvious to the user. From the unlatched configuration shown in FIG. 11B, the motor pack 76 is pushed toward the proximal chassis 74 with sufficient force to compress the compression spring 135 and latch the latch mechanism 78 to obtain the latched configuration shown in FIG. 11A. It has been observed that the flat proximal portion of the motor pack 76 surrounding the disengagement feature 82 is supportive enough to support the attached surgical tool 70 in an upright configuration. Thus, in some embodiments, such the upright configuration allows operator to rest the motor pack 76 on a sterile table for loading staple cartridges (in embodiments where the surgical tool 70 is a surgical stapler) and/or engage the surgical tool 70 into the motor pack 76 using a one-handed technique.

Figure 12A:
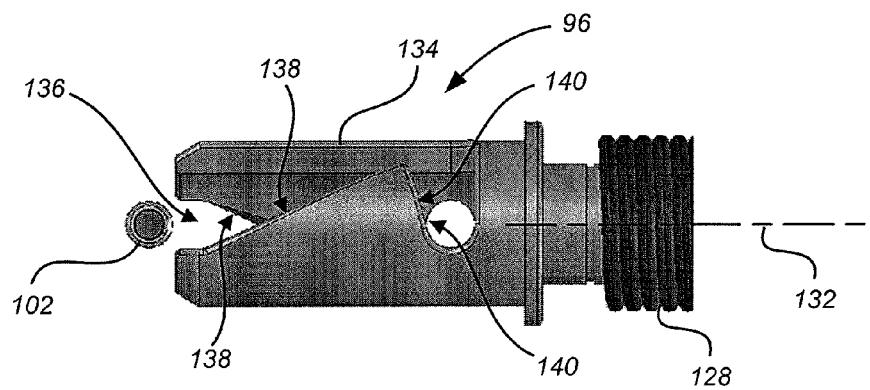
FIGS. 12A through 12E illustrate the operation of the latch mechanism of FIG. 11A from a pre-engagement configuration shown in FIG. 12A to an intermediate configuration shown in FIG. 12B to a retention configuration shown in FIG. 12C.
Figure 12B:
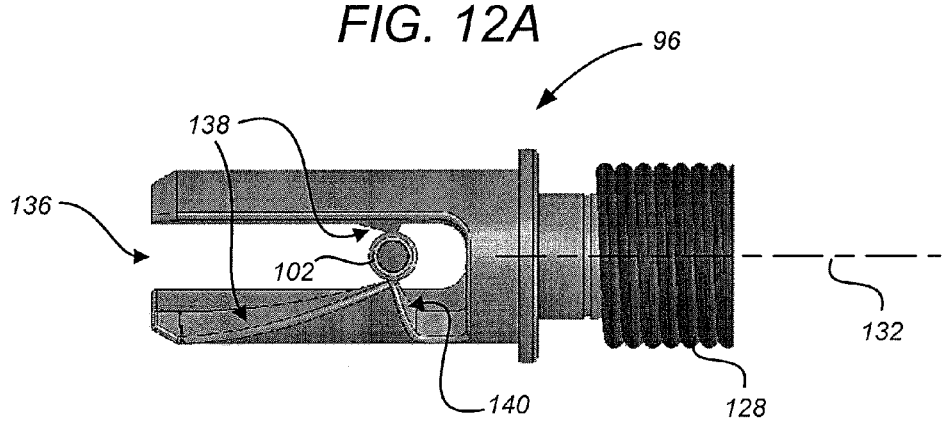
Figure 12C:
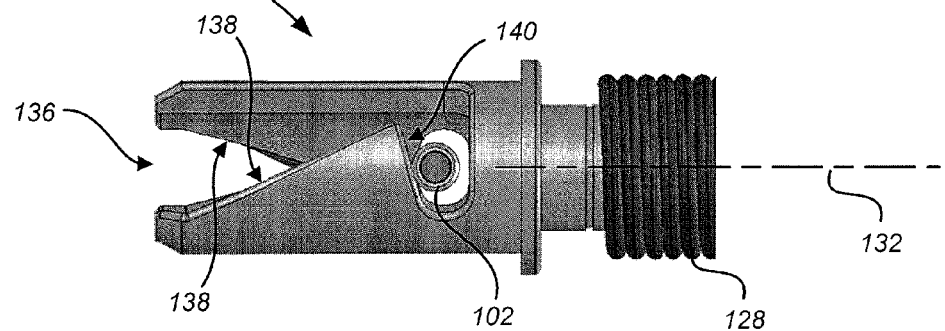
Figure 12D:
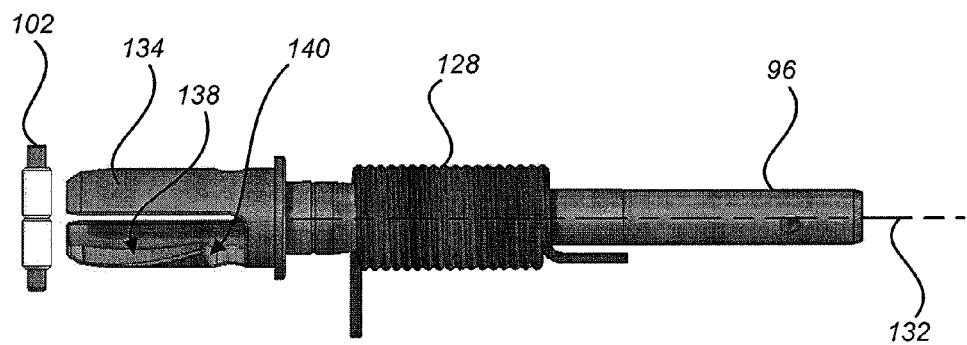
Figure 12E:
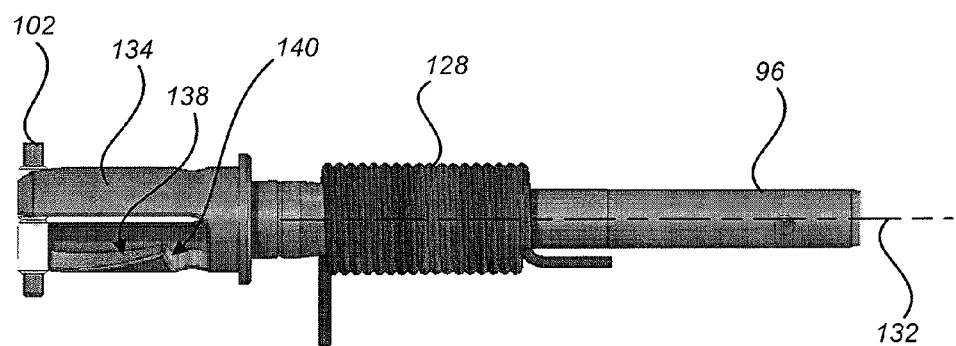

FIG. 12A through 12E illustrate an engagement sequence for the latch mechanism. The latch mechanism is configured to provide automatic latching in response to the motor pack 76 being pushed onto the proximal chassis 74. In FIG. 12A, the transverse latch member 102 and the latch shaft 96 are shown in a pre-engagement configuration at the start of the engagement sequence. In the embodiment described, the transverse latch member 102 is oriented vertically relative to the proximal chassis 74. The latch shaft 96 includes a cylindrical portion 134 that defines a slot 136 shaped to accommodate and interface with the transverse latch member 102 as the motor pack 76 is pushed onto the proximal chassis 74. The slot 136 defines two engagement cam surfaces 138 and two retention cam surfaces 140 that interface with the transverse latch member 102. From the pre-engagement configuration, relative movement of the motor pack 76 toward the proximal chassis 74 brings the transverse latch member 102 into the slot 136 and into contact with the engagement cam surfaces 138. Further relative movement of the motor pack 76 toward the proximal chassis 74 produces rotation of the latch shaft 96 in a first direction about the latch shaft axis 132 in response to contact between the transverse latch member 102 and the latch shaft 96. The rotation in the first direction continues until reaching an intermediate configuration illustrated in FIG. 12B in which the transverse latch member 102 reaches the proximal end of the engagement cam surfaces 138. From the intermediate configuration, additional relative movement of the motor pack 76 toward the proximal chassis 74 brings the transverse latch member 102 into contact with the retention cam surfaces 140 and results in rotation of the latch shaft opposite to the first direction into the configuration illustrated in FIG. 12C. The slope of the retention cam surfaces 140 relative to the latch shaft axis 132 combined with the torsion imparted by the torsion spring 128 results in the generation of a normal contact force between the transverse latch member 102 and the latch shaft 96. The normal contact force has a radial component reacted by the torsion spring 128 and an axial component that is aligned with the latch shaft axis 132, thereby providing a retaining tension force between the latch shaft 96 and the transverse latch member 102. To unlatch the latch mechanism, the latch shaft 96 is rotated in the first direction to disengage the retention cam surfaces 140 from the transverse latch member 102, thereby freeing the transverse latch member 102 from engagement with the latch shaft 96. Only one hand is required for manipulating the disengagement feature 82 to affect turning of the latch shaft 96, thus freeing the other hand for other tasks. FIGS. 12D and 12E shows a side view of the transverse latch member 102, as well as corresponding views of the latch shaft 96 and the torsion spring 128. FIG. 12D shows a pre-engagement arrangement. And FIG. 12E shows an initial engagement arrangement in which the transverse latch member 102 is in contact with an initial portion of the engagement cam surfaces 138.

Figure 13A:
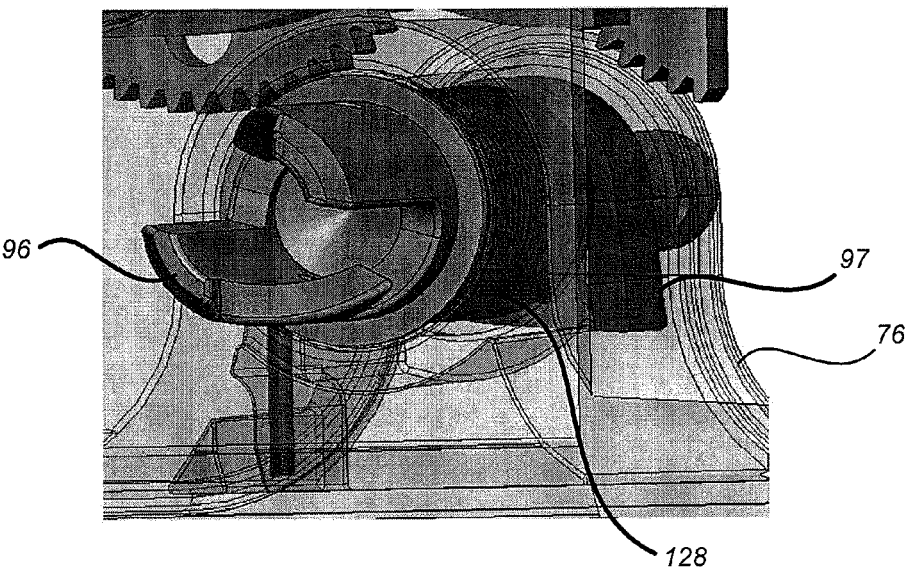
FIG. 13A is a partially-transparent perspective view of the motor pack further illustrating the latch mechanism of FIG. 11A.
Figure 13B:
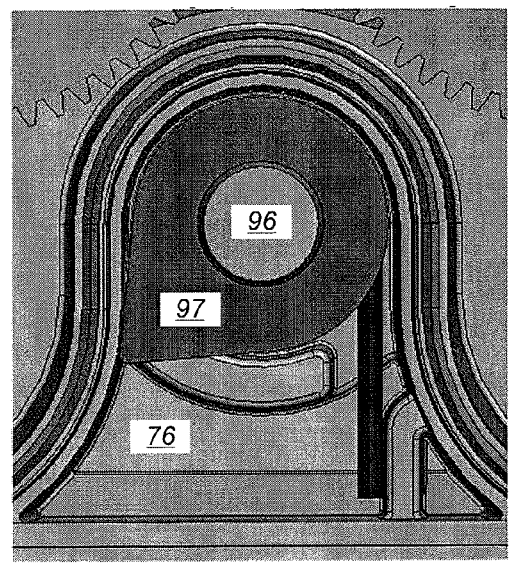
FIG. 13B is a rear view of the latch mechanism of FIG. 11A showing a clocking component interfacing with an inner wall of the motor pack housing to orient the latch mechanism in the pre-engagement configuration.

FIG. 13A shows a partially-transparent perspective view that illustrates interaction between the clocking component 97 and the motor pack 76 in the pre-engagement configuration of the latch mechanism 78. The clocking component 97 has a tear-drop shape. When the latch mechanism 78 is in the pre-engagement configuration, the clocking component 97 is held in contact with the housing of the motor pack 76 via torsion imparted by the torsion spring 128. The torsion spring 128 maintains the pre-engagement configuration of the latch mechanism 78 absent any other applied torque to the latch shaft 96 that would reorient the latch shaft 96 relative to the motor pack 76, such as interaction with the transverse latch member 102 or rotating of the disengagement feature 130. FIG. 13B shows a rear-view of the pre-engagement configuration of the latch mechanism 78 that further illustrates the contact between the attached clocking mechanism 97 and the motor pack housing inner wall.

Figure 14:
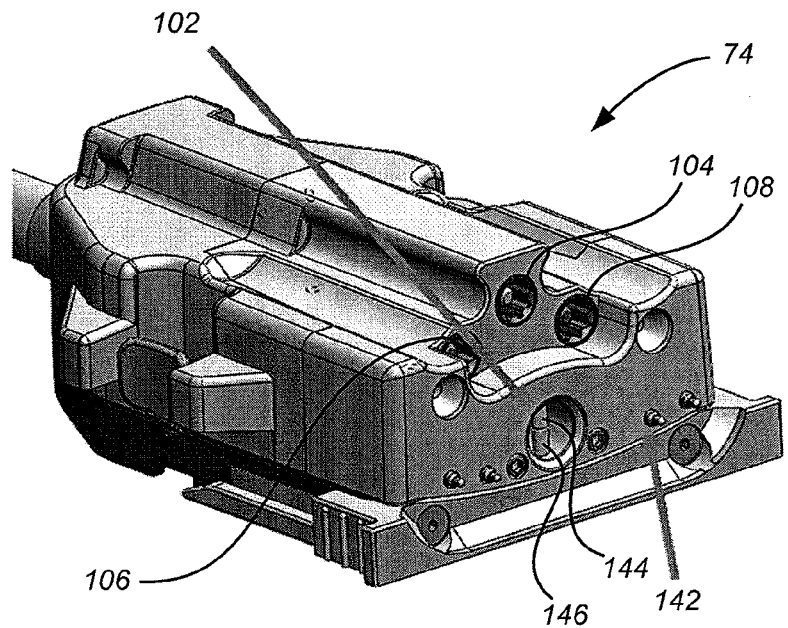
FIG. 14 is a perspective view of the proximal chassis of FIG. 6A showing a transverse latch member with rolling elements, motor pack electrical contacts, and actuation inputs.

FIG. 14 shows a perspective view of the proximal chassis 74 illustrating the transverse latch member 102, motor pack electrical contacts 142, and the proximal chassis actuation inputs 104, 106, 108. The transverse latch member 102 includes a first rolling element 144 and a second rolling element 146. The first and second rolling elements 144, 146 are disposed around a central supporting shaft and are configured to rotate independent of each other. Each of the first and second rolling elements 144, 146 interface with one of the engagement cam surfaces 138 during part of the movement of the motor pack 76 toward the proximal chassis 74 from the pre-engagement configuration shown in FIG. 12A to the intermediate configuration shown in FIG. 12B. Each of the first and second rolling elements 144, 146 interfaces with one of the retention cam surfaces 140 during the movement of the motor pack 76 toward the proximal chassis 74 from the intermediate configuration to the retention configuration shown in FIG. 12C. The use of the first and second rolling elements 144, 146 serves to reduce frictional resistance in the operation of the latch mechanism thereby making it easy to push mount the motor pack 76 onto the proximal chassis 74.

Figure 15:
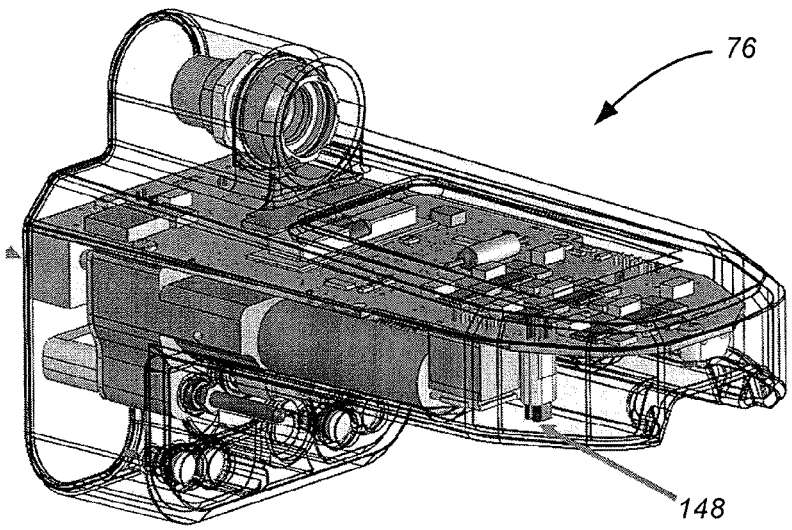
FIG. 15 is a partially-transparent perspective view of the motor pack of FIG. 6A showing hall sensors used to verify that the motor pack is mounted to the proximal chassis.

FIG. 15 shows hall sensor(s) 148 mounted to the motor pack 76. The hall sensor(s) 148 generate a signal(s) indicative of when the motor pack 76 is mounted to the proximal chassis 74. The proximal chassis 74 includes a sensor target(s) the proximity of which is detectable by the halls sensor(s) 148. The signal can be provided to a controller to communicate whether the motor pack 76 is mounted to the proximal chassis 74. In many embodiments, the signal indicates that the motor pack 76 is not mounted to the proximal chassis when a sufficient gap exists between the motor pack 76 and the proximal chassis 74, such as with the minimum gap 139 illustrated in FIG. 11B. It is also possible to use the motor pack electrical contacts 142 to supplement the information provided by the hall sensor(s) 148. There are also other suitable types of sensors that could be used in place of the halls sensor(s) 148, such as, but not limited to, a proximity sensor(s) and an optical sensor(s).

Other variations are within the spirit of the present invention. For example, the latch mechanism 78 can be reversed with the latch shaft 96 mounted in the proximal chassis 74 and the transverse latch member 102 mounted to the motor pack 76. The latch mechanism 78 can also be used in any other suitable application to latch a first assembly to a second assembly. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A robotic surgical assembly comprising:
an end effector including an articulated feature;
an elongate instrument shaft having a distal end supporting the end effector and a proximal end;
a chassis supporting the instrument shaft proximal end, the chassis being detachably mountable to a robotic arm; the chassis including an actuation input drivingly coupled with the end effector articulated feature;
a motor pack detachably mountable to the chassis, the motor pack including an actuation output that drivingly couples with the chassis actuation input when the motor pack is mounted to the chassis, the motor pack and the chassis having complementary-shaped interfaces providing sliding engagement between the motor pack and the chassis along an engagement axis; and
a latch mechanism configured to selectively retain the motor pack to the chassis, the latch mechanism including a latch shaft, a torsion spring; and a transverse latch member; the latch shaft being mounted to one of the motor pack or the chassis to rotate about a latch shaft axis; the torsion spring being operably coupled with the latch shaft to bias the latch shaft into a pre-engagement orientation relative to the one of the motor pack or the chassis when the motor pack is not mounted to the chassis, the transverse latch member being mounted to the other one of the motor pack or the chassis and oriented transverse to the latch shaft axis when the motor pack is slidingly engaged with the chassis along the engagement axis, the transverse latch member interfacing with the latch shaft to rotate the latch shaft about the latch shaft axis in a first rotational direction in response to relative movement of the motor pack toward the chassis along the engagement axis from a pre-engagement configuration to an intermediate configuration, the latch shaft being configured to rotate opposite to the first rotational direction in response to relative movement of the motor pack toward the chassis along the engagement axis from the intermediate configuration to a retention configuration, the latch shaft blocking movement of the transverse latch member in the retention configuration to restrain the motor pack from moving away from the chassis along the engagement axis.

2. The assembly of claim 1, wherein:
the latch shaft is mounted to the motor pack for rotation relative to the motor pack about the latch shaft axis;
the torsion spring is coupled with the motor pack; and
the transverse latch member is coupled with the chassis.

3. The assembly of claim 1, wherein:
the latch shaft is mounted to the chassis for rotation relative to the chassis about the latch shaft axis;
the torsion spring is coupled with the chassis; and
the transverse latch member is coupled with the motor pack.

4. The assembly of claim 1, wherein the latch shaft includes a cylindrical portion having a transverse slot configured to accommodate the transverse latch member and interface with the transverse latch member during at least part of the relative movement between the motor pack and the chassis along the engagement axis from the pre-engagement configuration through the intermediate configuration to the retention configuration.

5. The assembly of claim 4, wherein the transverse slot interfaces with the transverse latch member in the retention configuration to impart a force component to the transverse latch member along the latch shaft axis to retain the motor pack to the chassis.

6. The assembly of claim 1, wherein the transverse latch member includes a first rolling element that interfaces with the latch shaft via rolling contact.

7. The assembly of claim 6, wherein the transverse latch member includes a second rolling element that interfaces with the latch shaft via rolling contact, the first and second latch rolling elements being configured to rotate in different directions.

8. The assembly of claim 1, wherein the latch shaft interfaces with the transverse latch member in the retention configuration to impart a force component to the transverse latch member along the latch shaft axis to retain the motor pack to the chassis.

9. The assembly of claim 1, wherein the latch shaft axis and the engagement axis are parallel.

10. The assembly of claim 1, wherein the latch mechanism includes a disengagement feature operable to rotate the latch shaft in the first rotational direction to an orientation in which the motor pack can be moved relative to the chassis from the retention configuration to the intermediate configuration.

11. The assembly of claim 10, wherein the disengagement feature includes a hand rotatable member rotationally coupled with the latch shaft.

12. The assembly of claim 1, wherein at least one of the chassis actuation input or the motor pack actuation output includes a spring loaded coupling feature that accommodates an initial coupling misalignment between the chassis actuation input and the motor pack actuation output.

13. The assembly of claim 1, further comprising a sensor mounted to the motor pack or the chassis configured to generate a signal indicative of the motor pack being mounted to the chassis in the retention configuration.

14. The assembly of claim 1, further comprising an ejection mechanism configured to maintain at least a minimum gap between the motor pack and the chassis absent the motor pack and the chassis being pushed together by a force sufficient to reconfigure the ejection mechanism.

15. A latch mechanism to selectively prevent separation between a first assembly and a second assembly, the first and second assemblies having complementary-shaped interfaces providing sliding engagement between the first and second assemblies along an engagement axis, the latch mechanism comprising:

a latch shaft mounted to the first assembly to rotate about a latch shaft axis relative to the first assembly;
a torsion spring coupled with the latch shaft and the first assembly to bias the latch shaft into a pre-engagement orientation relative to the first assembly; and
a transverse latch member coupled with the second assembly, the transverse latch member being oriented transverse to the latch shaft axis when the first and second assemblies are slidingly engaged along the engagement axis, the transverse latch member interfacing with the latch shaft to rotate the latch shaft relative to the first assembly about the latch shaft axis in a first rotational direction in response to relative movement of the first assembly toward the second assembly along the engagement axis from a pre-engagement configuration to an intermediate configuration, the latch shaft being configured to rotate opposite to the first rotational direction relative to the first assembly in response to relative movement of the first assembly toward the second assembly from the intermediate configuration to a retention configuration, the latch shaft blocking movement of the transverse latch member in the retention configuration to restrain the first assembly from moving away from the second assembly along the engagement axis.

16. The latch mechanism of claim 15, wherein the latch shaft includes a cylindrical portion having a transverse slot configured to accommodate the transverse latch member and interface with the transverse latch member during at least part of the relative movement between the first and second assemblies along the engagement axis from the pre-engagement configuration through the intermediate configuration to the retention configuration.

17. The latch mechanism of claim 16, wherein the transverse slot interfaces with the transverse latch member in the retention configuration to impart a force component to the transverse latch member along the latch shaft axis to retain the first assembly to the second assembly.

18. The latch mechanism of claim 15, wherein the transverse latch mechanism includes a first rolling element that interfaces with the latch shaft via rolling contact.

19. The latch mechanism of claim 18, wherein the transverse latch member includes a second rolling element that interfaces with the latch shaft via rolling contact, the first and second latch rolling elements being configured to rotate in different directions.

20. The latch mechanism of claim 15, wherein the latch shaft interfaces with the transverse latch member in the retention configuration to impart a force component to the transverse latch member along the latch shaft axis to retain the first assembly to the second assembly.

21. The latch mechanism of claim 15, wherein the latch shaft axis and the engagement axis are parallel.

22. The latch mechanism of claim 15, wherein the latch mechanism includes a disengagement feature operable to rotate the latch shaft in the first rotational direction to an orientation in which the first assembly can be moved relative to the second assembly from the retention configuration to the intermediate configuration.

23. The latch mechanism of claim 22, wherein the disengagement feature includes a hand rotatable member rotationally coupled with the latch shaft.

24. The latch mechanism of claim 15, further comprising an ejection mechanism configured to maintain at least a minimum gap between the first and second assemblies absent the first and second assemblies being pushed together by a force sufficient to reconfigure the ejection mechanism.

* * * * *